(12) United States Patent
Martin et al.

(10) Patent No.: US 7,740,870 B2
(45) Date of Patent: *Jun. 22, 2010

(54) GROUP B STREPTOCOCCUS ANTIGENS AND CORRESPONDING DNA FRAGMENTS

(75) Inventors: Denis Martin, St.-Augustin-de-Desmaures (CA); Stéphane Rioux, Beauport (CA); Bernard R. Brodeur, Sillery (CA); Josée Hamel, Sillery (CA); Martine Boyer, Ste-Foy (CA)

(73) Assignee: ID Biomedical Corporation, Laval (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/135,911

(22) Filed: Jun. 9, 2008

(65) Prior Publication Data

US 2009/0042794 A1 Feb. 12, 2009

Related U.S. Application Data

(63) Continuation of application No. 10/482,929, filed as application No. PCT/CA02/01019 on Jul. 5, 2002, now Pat. No. 7,393,536.

(60) Provisional application No. 60/303,101, filed on Jul. 6, 2001.

(51) Int. Cl.
 *A61K 39/09* (2006.01)
(52) U.S. Cl. ............... 424/244.1; 424/243.1; 424/185.1; 424/190.1; 424/192.1; 530/350; 435/975
(58) Field of Classification Search ........................ None
 See application file for complete search history.

(56) References Cited

U.S. PATENT DOCUMENTS

2006/0210579 A1* 9/2006 Telford et al. ............ 424/190.1
2006/0210580 A1* 9/2006 Telford et al. ............ 424/190.1

FOREIGN PATENT DOCUMENTS

| WO | 94/06465 A1 | 3/1994 |
|---|---|---|
| WO | 99/13084 A1 | 3/1999 |
| WO | 00/39299 A2 | 7/2000 |
| WO | 01/32882 A2 | 5/2001 |
| WO | 02/34771 A2 | 5/2002 |
| WO | 02/092818 A2 | 11/2002 |
| WO | 03/054007 A2 | 7/2003 |

OTHER PUBLICATIONS

Bowie et al., "Deciphering the Message in Protein Sequences: Tolerance to Amino Acid Substitutions," *Science* 247:1306-1310, Mar. 16, 1990.

Fernandez-Espla et al., "*Streptococcus thermophilus* Cell Wall-Anchored Proteinase: Release, Purification, and Biochemical and Genetic Characterization," *Applied and Environmental Microbiology* 66(11):4772-4778, Nov. 2000.

Jameson et al., "The antigenic index: a novel algorithm for predicting antigenic determinants," *Computer Application Bioscience* 4(1):181-186, 1988.

Mikayama et al., "Molecular cloning and functional expression of a cDNA encoding glycosylation-inhibiting factor," *Proc. Natl. Acad. Sci. USA* 90:10056-10060, Nov. 1993.

Rudinger, "Characteristics of the amino acids as components of a peptide hormone sequence," *Peptide Hormones. Biol. Council.*, pp. 5-7, Jun. 1976.

Wan et al., "Epitope Map for a Growth Hormone Receptor Agonist Monoclonal Antibody, MAb 263," *Molecular Endocrinology* 17(11):2240-2250, 2003.

Hopp, "Retrospective: 12 Years of Antigenic Determinant Predictions, and More," *Peptide Research* 6(4):183-190, 1993.

Hofmann et al., "On the theoretical prediction of protein antigenic determinants from amino acid sequences," *Biomed. Biochim. Acta* 46(11):855-866, 1987.

Menendez-Arias et al., "A Basic microcomputer program for prediction of B and T cell epitopes in proteins," *Comput. Appl. Biosci.* 6(2):101-105, 1990.

Nakai et al., "PSORT: a program for detecting sorting signals in proteins and predicting their subcellular localization," *TIBS* 24:34-35, 1999.

Roitt et al., *Immunology*, 4th Edition, 1998, pp. 7.7-7.8, Mosby, London.

\* cited by examiner

*Primary Examiner*—Jennifer E Graser
(74) *Attorney, Agent, or Firm*—Seed IP Law Group PLLC

(57) ABSTRACT

The present invention relates to antigens, more particularly antigens of Group B *Streptococcus* (GBS) (*S. agalactiae*) which may be useful to prevent, diagnose and/or treat streptococcal infections.

12 Claims, 2 Drawing Sheets

Figure 1 (SEQ ID NO: 1)

```
   1 ATGTTACAAG AAAAGGAGAT TTTTATGAAC ACAAAACAGC GTTTTTCAAT CCGGAAATAT
  61 AAGTTAGGTG CCGTATCTGT ACTTTTGGGA ACCCTATTTT TTTTAGGCGG TATCACAAAT
 121 GTAGCTGCTG ATTCTGTCAT AAATAAGCCA TCTGATATTG CAGTTGAACA GCAAGTAAAA
 181 GACAGTCCAA CGAGCATAGC AAATGAGACA CCTACTAACA ACACGTCATC AGCCCTTGCG
 241 TCAACAGCTC AAGACAATCT TGTTACAAAG GCTAATAATA ATAGTCCAAC AGAAACACAA
 301 CCAGTAACTG AGCCTCACTC TCAAGCCACC GAGACATTTT CCCCAGCCGC AAATCAACCG
 361 GTTGAAAGCA CTCAAGAAGT TTCTAAAACT CCTTTAACCA AACAAAATTT AGCAGTCAAA
 421 CCTACACCAG CTATTTCTAA AGAAACCCCT CAAAACATTG ATAGTAATAA AATTATCACT
 481 GTCCCCAAAG TATGGAACAC AGGCTACAAA GGAGAGGGAA CTGTTGTAGC AATTATTGAC
 541 TCAGGACTAG ATACCAATCA CGATGCTCTC CAATTAAATG ATTCGACAAA AGCAAAATAC
 601 CAAAACGAAC AGCAAATGAA TGCTGCTAAA GCAAAGCTG GTATAAACTA TGGAAAATGG
 661 TATAACAACA AAGTAATCTT TGGTCACAAC TATGTTGATG TCAATACAGA GCTAAAAGAG
 721 GTGAAAAGCA CTTCTCATGG TATGCACGTA ACCAGTATCG CAACAGCTAA TCCTAGCAAG
 781 AAAGATACAA ATGAATTAAT CTATGGTGTT GCTCCTGAAG CACAAGTAAT GTTTATGAGA
 841 GTCTTCTCTG ATGAAAAAAG AGGAACTGGA CCAGCCCTTT ATGTTAAAGC TATTGAAGAT
 901 GCCGTTAAAC TCGGTGCTGA TAGCATTAAT TTAAGTTTAG GTGGAGCTAA TGGCTCTTTA
 961 GTTAATGCCG ATGACCGACT TATAAAAGCT TTAGAGATGG CTAGACTCGC TGGCGTTTCT
1021 GTTGTTATAG CAGCAGGTAA CGACGGTACA TTTGGGAGTG GAGCATCAAA GCCTTCTGCT
1081 CTTTATCCTG ATTATGGTTT AGTTGGTAGT CCATCAACAG CTCGTGAGGC CATTTCTGTA
1141 GCATCATATA ATAATACAAC ACTGGTTAAT AAAGTCTTCA ACATTATCGG ATTAGAAAAC
1201 AACAAAAATC TCAACAACGG ATTAGCTGCT TATGCAGATC CTAAAGTTAG TGATAAGACC
1261 TTTGAAGTAG GGAAGCAATA TGATTATGTT TTCGTAGGAA AAGGAAACGA CAATGATTAT
1321 AAGGACAAAA CTTTAAATGG TAAAATCGCC TTAATTGAAC GTGGAGATAT TACTTTTACA
1381 AAAAAAGTCG TCAACGCTAT TAATCACGGT GCTGTGGGGA CTATTATCTT TAATAACAAA
1441 GCTGGAGAAG CTAATCTAAC AATGAGTTTA GATCCTGAAG CAAGCGCTAT TCCTGCCATT
1501 TTTACTCAAA AAGAGTTTGG AGATGTTTTA GCTAAAAACA ACTATAAAAT TGTATTTAAC
1561 AATATCAAAA ATAAACAAGC CAACCCTAAT GCAGGTGTCC TATCTGACTT TTCAAGCTGG
1621 GGATTAACAG CAGACGGACA ATTAAAACCT GACTTATCTG CTCCTGGAGG CTCTATTTAC
1681 GCCGCTATCA ATGATAATGA ATATGATATG ATGAGTGGGA CAAGTATGGC TTCTCCCCAT
1741 GTCGCTGGTG CTACTGCTCT AGTTAAACAA TACTTATTGA AGAACATCC AGAACTTAAA
1801 AAAGGTGACA TTGAAAGAAC TGTCAAATAC CTTCTTATGA GTACTGCTAA AGCACACCTA
1861 AACAAAGATA CAGGCGCTTA CACCTCACCA CGCCAACAAG GAGCAGGTAT TATCGATGTC
1921 GCAGCAGCAG TTCAGACAGG ATTATACCTA ACTGGTGGGG AAAACAACTA TGGTAGCGTT
1981 ACATTAGGAA ATATTAAAGA TAAAATTTCC TTTGATGTTA CTGTTCATAA TATCAATAAA
2041 GTTGCAAAAG ATTTACACTA TACAACCTAT TTAAATACTG ATCAAGTTAA AGATGGCTTT
2101 GTCACATTAG CTCCTCAACA ACTTGGTACA TTTACAGGGA AAACGATACG GATTGAACCA
2161 GGGCAAACTA AAACGATTAC AATTGATATA GATGTTTCGA ATACCATGA CATGTTAAAA
2221 AAAGTAATGC CAAACGGCTA TTTCCTAGAA GGCTACGTAC GTTTTACAGA CCCTGTTGAT
2281 GGTGGGGAAG TTCTTAGTAT TCCTTATGTT GGATTTAAGG GAGAATTCCA AAACTTAGAA
2341 GTTTTAGAAA AATCCATTTA TAAGCTTGTT GCTAACAAAG AAAAGGGATT TTATTTCCAA
2401 CCGAAACAAA CAAACGAAGT TCCTGGTTCA GAAGATTATA CTGCCTTAAT GACTACAAGT
2461 TCAGAGCCTA TCTACTCAAC AGACGGTACT AGTCCTATCC AATTGAAAGC CTTGGGAAGC
2521 TATAAGTCTA TAGATGGAAA ATGGATCTTA CAACTAGAGC AAAAAGGCCA GCCTCATCTA
2581 GCCATTTCAC CTAATGATGA CCAAAATCAA GATGCCGTTG CACTGAAAGG TGTTTTCTTA
2641 CGTAATTTCA ATAATTTAAG AGCCAAAGTC TATCGTGCAG ATGATGTTAA TTTACAAAAA
2701 CCACTATGGG TAAGTGCTCC CCAAGCAGGA GATAAAAATT ACTACAGCGG AAATACTGAA
2761 AATCCAAAAT CTACATTTTT ATATGACACA GAATGGAAAG GAACCACTAC TGATGGTATT
2821 CCTTTAGAAG ATGGAAAATA CAAATACGTT TAACATACT ACTCTGATGT CCCTGGCTCT
2881 AAGCCACAAC AAATGGTATT TGATATCACT TTGGATAGAC AAGCTCCTAC ACTAACAACA
2941 GCAACTTATG ACAAGATAG ACGTATCTTC AAAGCTCGTC CTGCAGTAGA ACACGGGGAA
3001 TCTGGTATCT TTAGAGAACA AGTTTTTTAC TTAAAAAAAG ATAAAGATGG TCATTATAAT
3061 AGCGTCTTAC GTCAAAAAGG AGAAGACGGT ATCCTTGTTG AAGATAACAA AGTATTTATC
3121 AAACAAGAAA AGGATGGTAC CTTTATTCTA CCTAAAGAGG TTAATGATTT CTCTCATGTC
3181 TACTACACTG TTGAAGATTA TGCAGGCAAT CTAGTGTCAG CAAAACTCGA AGATTTGATC
3241 AATATTGGCA ATAAAAATGG TTTAGTAAAC GTCAAAGTGT TTAGCCCTGA GCTTAACAGT
3301 AATGTCGATA TTGATTTCTC TTACTCTGTC AAAGATGACA AAGGTAATGT CATCAAAAAG
3361 CAACATCACG GAAAGACCT CAATTTACTG AAATTGCCTT TGGTACCTA TACGTTTGAC
3421 CTATTCTTAT ACGATGAGGA ACGAGCAAAT CTAATCAGTC CCCAAAGTGT CACTGTAACT
3481 ATTTCTGAAA AAGATAGCCT TAAAGACGTC TTATTTAAAG TTAACTTACT CAAGAAAGCA
3541 GCCTTACTCG TTGAATTTGA CAAGCTTTTA CCAAAAGGAG CAACAGTCCA GTTGGTTACT
```

Figure 1 (SEQ ID NO: 1) (continued)

```
3601 AAGACAAATA CTGTTGTTGA TCTACCAAAA GCAACTTATT CTCCTACTGA CTATGGTAAA
3661 AACATACCTG TAGGAGACTA TCGTTTAAAC GTAACGCTGC CTAGTGGGTA TAGCACTTTA
3721 GAGAACTTAG ATGATTACT TGTATCCGTA AAAGAAGGTC AAGTAAATCT AACAAAATTG
3781 ACGCTGATTA ATAAAGCTCC TCTAATTAAT GCCCTAGCAG AACAAACTGA CATTATTTCC
3841 CAACCTGTGT TTTATAATGC TGGAACTCAC TTAAAAAATA ATTACCTAGC TAATCTTGAA
3901 AAGGCACAAA CTTTAATTAA AAATAGAGTG GAACAAACAA GTATTGATAA TGCTATTGCT
3961 GCTTTGAGAG AAAGTCGCCA AGCTCTTAAC GGTAAAGAAA CAGATACTTC TTTACTGGCA
4021 AAAGCTATTT TAGCTGAAAC AGAAATCAAG GGAAACTATC AATTTGTTAA TGCTAGTCCA
4081 TTAAGCCAAT CAACTTATAT CAATCAAGTC CAATTGGCGA AAAATCTTCT ACAAAAACCT
4141 AACGTCACTC AATCAGAAGT AGACAAAGCC TTAGAAAATC TTGATATTGC TAAAAATCAA
4201 TTAAATGGTC ATGAAACTGA TTACTCTGGT TTACACCATA TGATAATTAA AGCAAATGTT
4261 CTGAAACAAA CATCATCTAA ATATCAGAAC GCCAGTCAAT TTGCTAAAGA AAATTATAAT
4321 AACCTTATCA AGAAAGCAGA ATTGCTGCTT TCCAATAGAC AAGCTACACA AGCTCAAGTT
4381 GAAGAGTTAT AAACCAAAT AAAAGCAACC GAACAAGAAC TTGATGGTCG CGATAGAGTT
4441 TCTTCCGCAG AGAATTATAG TCAATCACTC AATGATAATG ACTCTCTCAA TACCACACCT
4501 ATCAATCCGC CAAATCAGCC CCAGGCGTTG ATATTCAAAA AAGGCATGAC TAAAGAAAGT
4561 GAGGTTGCTC AGAAGCGTGT CTTAGGGGTG ACTAGCCAAA CCGATAATCA AAAGATAAAG
4621 ACAAACAAGC TTCCTAAAAC AGGCGAAAGC ACTCCTAAAA TAACCTATAC AATATTGCTA
4681 TTTAGTCTCT CTATGCTAGG TCTGGCAACA ATCAAACTAA AGTCTATCAA AAGAGAATAA
```

Figure 2 (SEQ ID NO: 2)

```
   1 MLQEKEIFMN TKQRFSIRKY KLGAVSVLLG TLFFLGGITN VAADSVINKP SDIAVEQQVK
  61 DSPTSIANET PTNNTSSALA STAQDNLVTK ANNNSPTETQ PVTEPHSQAT ETFSPAANQP
 121 VESTQEVSKT PLTKQNLAVK PTPAISKETP QNIDSNKIIT VPKVWNTGYK GRGTVVAIID
 181 SGLDTNHDAL QLNDSTKAKY QNEQQMNAAK AKAGINYGKW YNNKVIFGHN YVDVNTELKE
 241 VKSTSHGMHV TSIATANPSK KDTNELIYGV APEAQVMFMR VFSDEKRGTG PALYVKAIED
 301 AVKLGADSIN LSLGGANGSL VNADDRLIKA LEMARLAGVS VVIAAGNDGT FGSGASKPSA
 361 LYPDYGLVGS PSTAREAISV ASYNNTTLVN KVFNIIGLEN NKNLNNGLAA YADPKVSDKT
 421 FEVGKQYDYV FVGKGNDNDY KDKTLNGKIA LIERGDITFT KKVVNAINHG AVGAIIFNNK
 481 AGEANLTMSL DPEASAIPAI FTQKEFGDVL AKNNYKIVFN NIKNKQANPN AGVLSDFSSW
 541 GLTADGQLKP DLSAPGGSIY AAINDNEYDM MSGTSMASPH VAGATALVKQ YLLKEHPELK
 601 KGDIERTVKY LLMSTAKAHL NKDTGAYTSP RQQGAGIIDV AAAVQTGLYL TGGENNYGSV
 661 TLGNIKDKIS FDVTVHNINK VAKDLHYTTY LNTDQVKDGF VTLAPQQLGT FTGKTIRIEP
 721 GQTKTITIDI DVSKYHDMLK KVMPNGYFLE GYVRFTDPVD GGEVLSIPYV GFKGEFQNLE
 781 VLEKSIYKLV ANKEKGFYFQ PKQTNEVPGS EDYTALMTTS SEPIYSTDGT SPIQLKALGS
 841 YKSIDGKWIL QLEQKGQPHL AISPNDDQNQ DAVALKGVFL RNFNNLRAKV YRADDVNLQK
 901 PLWVSAPQAG DKNYYSGNTE NPKSTFLYDT EWKGTTTDGI PLEDGKYKYV LTYYSDVPGS
 961 KPQQMVFDIT LDRQAPTLTT ATYDKDRRIF KARPAVEHGE SGIFREQVFY LKKDKDGHYN
1021 SVLRQKGEDG ILVEDNKVFI KQEKDGSFIL PKEVNDFSHV YYTVEDYAGN LVSAKLEDLI
1081 NIGNKNGLVN VKVFSPELNS NVDIDFSYSV KDDKGNVIKK QHHGKDLNLL KLPFGTYTFD
1141 LFLYDEERAN LISPQSVTVT ISEKDSLKDV LFKVNLLKKA ALLVEFDKLL PKGATVQLVT
1201 KTNTVVDLPK ATYSPTDYGK NIPVGDYRLN VTLPSGYSTL ENLDDLLVSV KEGQVNLTKL
1261 TLINKAPLIN ALAEQTDIIS QPVFYNAGTH LKNNYLANLE KAQTLIKNRV EQTSIDNAIA
1321 ALRESRQALN GKETDTSLLA KAILAETEIK GNYQFVNASP LSQSTYINQV QLAKNLLQKP
1381 NVTQSEVDKA LENLDIAKNQ LNGHETDYSG LHHMIIKANV LKQTSSKYQN ASQFAKENYN
1441 NLIKKAELLL SNRQATQAQV EELLNQIKAT EQELDGRDRV SSAENYSQSL NDNDSLNTTP
1501 INPPNQPQAL IFKKGMTKES EVAQKRVLGV TSQTDNQKIK TNKLPKTGES TPKITYTILL
1561 FSLSMLGLAT IKLKSIKRE*
```

GROUP B STREPTOCOCCUS ANTIGENS AND CORRESPONDING DNA FRAGMENTS

CROSS-REFERENCE TO RELATED APPLICATIONS

This application is a continuation of U.S. patent application Ser. No. 10/482,929, now allowed, which has a filing date of Jul. 16, 2004, and which is a national stage application filed under 35 U.S.C. §371 of International Patent Application PCT/CA02/01019, accorded an international filing date of Jul. 5, 2002, which claims the benefit U.S. Provisional Application No. 60/303,101, filed Jul. 6, 2001, all of which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112_427C1_SEQUENCE_LISTING.txt. The text file is 22 KB, was created on Jun. 9, 2008, and is being submitted electronically via EFS-Web.

FIELD OF THE INVENTION

The present invention is related to polypeptides of Group B *Streptococcus* (GBS) (*S. agalactiae*) which may be used to prevent, diagnose, and/or treat GBS infections.

BACKGROUND OF THE INVENTION

*Streptococcus* are gram (+) bacteria that are differentiated by group specific carbohydrate antigens A through O found on their cell surface. *Streptococcus* groups are further distinguished by type-specific capsular polysaccharide antigens. Several serotypes have been identified for the GBS: Ia, Ib, II, III, IV, V, VI, VII and VIII. GBS also contains antigenic proteins known as "C-proteins" (alpha, beta, gamma and delta), some of which have been cloned.

Although GBS is a common component of the normal human vaginal and colonic flora this pathogen has long been recognized as a major cause of infections in neonates, expectant mothers, some non-pregnant adults as well as mastitis in dairy herds. Expectant mothers exposed to GBS are at risk of postpartum infection and may transfer the infection to their baby as the child passes through the birth canal.

GBS infections in infants are restricted to very early infancy. Approximately 80% of infant infections occur in the first days of life, so-called early-onset disease. Late-onset infections occur in infants between 1 week and 2 to 3 months of age. Clinical syndromes of GBS disease in newborns include sepsis, meningitis, pneumonia, cellulitis, osteomyelitis, septic arthritis, endocarditis and epiglottis. In addition to acute illness due to GBS, which is itself costly, GBS infections in newborns can result in death, disability, and, in rare instances, recurrence of infection. Although the organism is sensitive to antibiotics, the high attack rate and rapid onset of sepsis in neonates and meningitis in infants results in high morbidity and mortality.

Among pregnant women, GBS causes clinical illness ranging from mild urinary tract infection to life-threatening sepsis and meningitis, including also osteomyelitis, endocarditis, amnionitis, endometritis, wound infections (postcesarean and postepisiotomy), cellulitis, fasciitis.

Among non-pregnant adults, the clinical presentations of invasive GBS disease most often take the form of primary bacteremia but also skin or soft tissue infection, pneumonia, urosepsis, endocarditis, peritonitis, meningitis, empyema. Skin or soft tissue infections include cellulitis, infected peripheral ulcers, osteomyelitis, septic arthritis and decubiti or wound infections. Among people at risk, there are debilitated hosts such as people with a chronic disease such as diabetes mellitus and cancer, or elderly people.

GBS infections can also occur in animals and cause mastitis in dairy herds.

Type-specific polysaccharides have proven to be poorly immunogenic in hosts and are restricted to the particular serotype from which the polysaccharide originates. Further, capsular polysaccharide elicit a T cell independent response i.e., no IgG production. Consequently capsular polysaccharide antigens are unsuitable as a vaccine component for protection against GBS infection.

Others have focused on the C-protein beta antigen which demonstrated immunogenic properties in mice and rabbit models. This protein was found to be unsuitable as a human vaccine because of its undesirable property of interacting with high affinity and in a non-immunogenic manner with the Fc region of human IgA. The C-protein alpha antigen is rare in type III serotypes of GBS which is the serotype responsible for most GBS mediated conditions and is therefore of little use as a vaccine component.

There remains an unmet need for GBS polypeptides which may be used to prevent, diagnose and/or treat GBS infection.

SUMMARY OF THE INVENTION

According to one aspect, the present invention provides an isolated polynucleotide encoding a polypeptide having at least 80% identity to a second polypeptide comprising a sequence chosen from SEQ ID No: 2 or fragments or analogs thereof.

According to one aspect, the present invention relates to polypeptides comprising SEQ ID No: 2 or fragments or analogs thereof.

In other aspects, there are provided polypeptides encoded by polynucleotides of the invention, pharmaceutical composition, vectors comprising polynucleotides of the invention operably linked to an expression control region, as well as host cells transfected with said vectors and processes for producing polypeptides comprising culturing said host cells under conditions suitable for expression.

BRIEF DESCRIPTION OF THE DRAWINGS

FIG. 1 represents the DNA sequence of BVH-A5 gene from serotype III Group B *Streptococcus* strain NCS 954; (SEQ ID NO: 1). The underlined portion of the sequence represents the region coding for the leader peptide.

FIG. 2 represents the amino acid sequence of BVH-A5 polypeptide from serotype III Group B *Streptococcus* strain NCS 954; (SEQ ID NO: 2). The underlined sequence represents the 43 amino acid residues leader peptide.

DETAILED DESCRIPTION OF THE INVENTION

The present invention provides purified and isolated polynucleotides, which encode Streptococcal polypeptides that may be used to prevent, diagnose and/or treat Streptococcal infection.

According to one aspect, the present invention provides an isolated polynucleotide encoding a polypeptide having at least 80% identity to a second polypeptide comprising a sequence chosen from SEQ ID NO: 2 or fragments or analogs thereof.

According to one aspect, the present invention provides an isolated polynucleotide encoding a polypeptide having at least 80% identity to a second polypeptide comprising a sequence chosen from SEQ ID NO: 2 or fragments or analogs thereof.

According to one aspect, the present invention provides an isolated polynucleotide encoding a polypeptide having at least 90% identity to a second polypeptide comprising a sequence chosen from SEQ ID NO: 2 or fragments or analogs thereof.

According to one aspect, the present invention provides an isolated polynucleotide encoding a polypeptide having at least 95% identity to a second polypeptide comprising a sequence chosen from SEQ ID NO: 2 or fragments or analogs thereof.

According to one aspect, the present invention provides an isolated polynucleotide encoding a polypeptide having at least 98% identity to a second polypeptide comprising a sequence chosen from SEQ ID NO: 2 or fragments or analogs thereof.

According to one aspect, the present invention relates to polypeptides comprising an amino acid sequence selected from SEQ ID No: 2 or fragments or analogs thereof.

According to one aspect, the present invention relates to polypeptides characterized by the amino acid sequence SEQ ID NO: 2 or fragments or analogs thereof.

According to one aspect, the present invention provides a polynucleotide encoding an epitope bearing portion of a polypeptide comprising SEQ ID NO: 2 or fragments or analogs thereof.

According to one aspect, the present invention relates to epitope bearing portions of a polypeptide comprising SEQ ID NO: 2 or fragments or analogs thereof.

According to one aspect, the present invention provides an isolated polynucleotide encoding a polypeptide having at least 80% identity to a second polypeptide comprising SEQ ID NO: 2.

According to one aspect, the present invention provides an isolated polynucleotide encoding a polypeptide having at least 90% identity to a second polypeptide comprising SEQ ID NO: 2.

According to one aspect, the present invention provides an isolated polynucleotide encoding a polypeptide having at least 95% identity to a second polypeptide comprising SEQ ID NO: 2.

According to one aspect, the present invention provides an isolated polynucleotide encoding a polypeptide having at least 98% identity to a second polypeptide comprising SEQ ID NO: 2.

According to one aspect, the present invention relates to polypeptides comprising SEQ ID NO: 2.

According to one aspect, the present invention relates to polypeptides characterized by the amino acid sequence SEQ ID NO: 2.

According to one aspect, the present invention provides a polynucleotide encoding an epitope bearing portion of a polypeptide comprising SEQ ID NO: 2.

According to one aspect, the present invention relates to epitope bearing portions of a polypeptide comprising SEQ ID NO: 2.

According to one aspect, the present invention provides an isolated polynucleotide comprising a polynucleotide chosen from:

(a) a polynucleotide encoding a polypeptide having at least 80% identity to a second polypeptide comprising a sequence chosen from: SEQ ID NO: 2 or fragments or analogs thereof;

(b) a polynucleotide encoding a polypeptide having at least 95% identity to a second polypeptide comprising a sequence chosen from: SEQ ID NO: 2 or fragments or analogs thereof;

(c) a polynucleotide encoding a polypeptide comprising a sequence chosen from: SEQ ID NO: 2 or fragments or analogs thereof;

(d) a polynucleotide encoding a polypeptide capable of raising antibodies having binding specificity for a polypeptide comprising a sequence chosen from: SEQ ID NO:2 or fragments or analogs thereof;

(e) a polynucleotide encoding an epitope bearing portion of a polypeptide comprising a sequence chosen from SEQ ID NO: 2 or fragments or analogs thereof;

(f) a polynucleotide comprising a sequence chosen from SEQ ID NO: 1 or fragments or analogs thereof;

(g) a polynucleotide that is complementary to a polynucleotide in (a), (b), (c), (d), (e) or (f).

According to one aspect, the present invention provides an isolated polynucleotide comprising a polynucleotide chosen from:

(a) a polynucleotide encoding a polypeptide having at least 80% identity to a second polypeptide comprising a sequence chosen from: SEQ ID NO: 2;

(b) a polynucleotide encoding a polypeptide having at least 95% identity to a second polypeptide comprising a sequence chosen from: SEQ ID NO: 2;

(c) a polynucleotide encoding a polypeptide comprising a sequence chosen from: SEQ ID NO: 2;

(d) polynucleotide encoding a polypeptide capable of raising antibodies having binding specificity for a polypeptide comprising a sequence chosen from: SEQ ID NO: 2;

(e) a polynucleotide encoding an epitope bearing portion of a polypeptide comprising a sequence chosen from SEQ ID NO: 2;

(f) a polynucleotide comprising a sequence chosen from SEQ ID NO: 1;

(g) a polynucleotide that is complementary to a polynucleotide in (a), (b), (c), (d), (e) or (f).

According to one aspect, the present invention provides an isolated polypeptide comprising a polypeptide chosen from:

(a) a polypeptide having at least 80% identity to a second polypeptide comprising SEQ ID NO: 2 or fragments or analogs thereof;

(b) a polypeptide having at least 95% identity to a second polypeptide comprising SEQ ID NO: 2 or fragments or analogs thereof;

(c) a polypeptide comprising SEQ ID NO: 2 or fragments or analogs thereof;

(d) a polypeptide capable of raising antibodies having binding specificity for a polypeptide comprising SEQ ID NO: 2 or fragments or analogs thereof;

(e) an epitope bearing portion of a polypeptide comprising SEQ ID NO: 2 or fragments or analogs thereof;

(f) the polypeptide of (a), (b), (c), (d), or (e) wherein the N-terminal Met residue is deleted;

(g) the polypeptide of (a), (b), (c), (d), or (e) wherein the secretory amino acid sequence is deleted.

According to one aspect, the present invention provides an isolated polypeptide comprising a polypeptide chosen from:

(a) a polypeptide having at least 80% identity to a second polypeptide comprising SEQ ID NO: 2;

(b) a polypeptide having at least 95% identity to a second polypeptide comprising SEQ ID NO: 2;

(c) a polypeptide comprising SEQ ID NO: 2;

(d) a polypeptide capable of raising antibodies having binding specificity for a polypeptide comprising SEQ ID NO: 2;

(e) an epitope bearing portion of a polypeptide comprising SEQ ID NO: 2;

(f) the polypeptide of (a), (b), (c), (d), or (e) wherein the N-terminal Met residue is deleted;

(g) the polypeptide of (a), (b), (c), (d), or (e) wherein the secretory amino acid sequence is deleted.

Those skilled in the art will appreciate that the invention includes DNA molecules, i.e. polynucleotides and their complementary sequences that encode analogs such as mutants, variants, analogues and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

In accordance with the present invention, all polynucleotides encoding polypeptides of the present invention are within the scope of the present invention.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample, which naturally includes the selected peptide. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 80% identity with those sequences illustrated in the figures or fragments thereof. That is, 80% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:

ala, pro, gly, gln, asn, ser, thr, val;
cys, ser, tyr, thr;
val, ile, leu, met, ala, phe;
lys, arg, orn, his; and
phe, tyr, trp, his.

The preferred substitutions also include substitutions of D-enantiomers for the corresponding L-amino acids.

In an alternative approach, the analogs could be fusion proteins, incorporating moieties which render purification easier, for example by effectively tagging the desired polypeptide. It may be necessary to remove the "tag" or it may be the case that the fusion polypeptide itself retains sufficient antigenicity to be useful.

The percentage of homology is defined as the sum of the percentage of identity plus the percentage of similarity or conservation of amino acid type.

In one embodiment, analogs of polypeptides of the invention will have about 80% identity with those sequences illustrated in the figures or fragments thereof. That is, 80% of the residues are the same. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

In one embodiment, analogs of polypeptides of the invention will have about 80% homology with those sequences illustrated in the figures or fragments thereof. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTX will align the longest stretch of similar sequences and assign a value to the fit. It is thus possible to obtain a comparison where several regions of similarity are found, each having a different score. Both types of identity analysis are contemplated in the present invention.

In an alternative approach, the analogs or derivatives could be fusion polypeptides, incorporating moieties which render purification easier, for example by effectively tagging the desired protein or polypeptide, it may be necessary to remove the "tag" or it may be the case that the fusion polypeptide itself retains sufficient antigenicity to be useful.

It is well known that it is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties.

Thus, what is important for analogs, derivatives and fragments is that they possess at least a degree of the antigenicity/immunogenicity of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *Streptococcus* strains.

Moreover, the polypeptides of the present invention can be modified by terminal —NH$_2$ acylation (e.g., by acetylation, or thioglycolic acid amidation, terminal carboxy amidation, e.g., with ammonia or methylamine) to provide stability, increased hydrophobicity for linking or binding to a support or other molecule.

Also contemplated are hetero and homo polypeptide multimers of the polypeptide fragments and analogs. These polymeric forms include, for example, one or more polypeptides that have been cross-linked with cross-linkers such as avidin/biotin, gluteraldehyde or dimethyl-superimidate. Such polymeric forms also include polypeptides containing two or more tandem or inverted contiguous sequences, produced from multicistronic mRNAs generated by recombinant DNA technology.

In a further embodiment, the present invention also relates to chimeric polypeptides which comprise one or more polypeptides or fragments or analogs thereof as defined in the figures of the present application.

In a further embodiment, the present invention also relates to chimeric polypeptides comprising two or more polypeptides having a sequence chosen from SEQ ID NO: 2 or fragments or analogs thereof; provided that the polypeptides are linked as to formed a chimeric polypeptide.

In a further embodiment, the present invention also relates to chimeric polypeptides comprising two or more polypeptides having a sequence chosen from SEQ ID NO: 2 provided that the polypeptides are linked as to formed a chimeric polypeptide. Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a methionine (Met) or valine (Val) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a streptococcal culture and subsequently sequenced to determine the initial residue of the mature protein and therefore the sequence of the mature polypeptide.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington D.C., p. 109-143).

According to another aspect of the invention, there are also provided (i) a composition of matter containing a polypeptide of the invention, together with a carrier, diluent or adjuvant; (ii) a pharmaceutical composition comprising a polypeptide of the invention and a carrier, diluent or adjuvant; (iii) a vaccine comprising a polypeptide of the invention and a carrier, diluent or adjuvant; (iv) a method for inducing an immune response against *Streptococcus*, in a host, by administering to the host, an immunogenically effective amount of a polypeptide of the invention to elicit an immune response, e.g., a protective immune response to *Streptococcus*; and particularly, (v) a method for preventing and/or treating a *Streptococcus* infection, by administering a prophylactic or therapeutic amount of a polypeptide of the invention to a host in need.

According to another aspect of the invention, there are also provided (i) a composition of matter containing a polynucleotide of the invention, together with a carrier, diluent or adjuvant; (ii) a pharmaceutical composition comprising a polynucleotide of the invention and a carrier, diluent or adjuvant; (iii) a method for inducing an immune response against *Streptococcus*, in a host, by administering to the host, an immunogenically effective amount of a polynucleotide of the invention to elicit an immune response, e.g., a protective immune response to *Streptococcus*; and particularly, (iv) a method for preventing and/or treating a *Streptococcus* infection, by administering a prophylactic or therapeutic amount of a polynucleotide of the invention to a host in need.

Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol. 19 (ed.) Burdou, R. H. & Van Knippenberg P. H. (1988), Elsevier N.Y.

According to another aspect, there are provided pharmaceutical compositions comprising one or more Streptococcal polypeptides of the invention in a mixture with a pharmaceutically acceptable adjuvant. Suitable adjuvants include (1) oil-in-water emulsion formulations such as MF59™, SAF™, Ribi™; (2) Freund's complete or incomplete adjuvant; (3) salts i.e. AlK(SO$_4$)$_2$, AlNa(SO$_4$)$_2$, AlNH$_4$(SO$_4$)$_2$, Al(OH)$_3$, AlPO$_4$, silica, kaolin; (4) saponin derivatives such as Stimulon™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides i.e. poly IC and poly AU, detoxified cholera toxin (CTB) and E. coli heat labile toxin for induction of mucosal immunity. A more detailed description of adjuvant is available in a review by M. Z. I. Khan et al. in *Pharmaceutical Research*, vol. 11, No. 1 (1994) pp 2-11, and also in another review by Gupta et al., in *Vaccine*, Vol. 13, No. 14, pp 1263-1276 (1995) and in WO 99/24578. Preferred adjuvants include QuilA™, QS21™, Alhydrogel™ and Adjuphos™.

Pharmaceutical compositions of the invention may be administered parenterally by injection, rapid infusion, nasopharyngeal absorption, dermoabsorption, or buccal or oral.

The term pharmaceutical composition is also meant to include antibodies. In accordance with the present invention, there is also provided the use of one or more antibodies having binding specificity for the polypeptides of the present invention for the treatment or prophylaxis of *Streptococcus* infection and/or diseases and symptoms mediated by *Streptococcus* infection.

Pharmaceutical compositions of the invention are used for the prophylaxis or treatment of streptococcal infection and/or diseases and symptoms mediated by streptococcal infection as described in Manual of Clinical Microbiology, P. R. Murray (Ed, in chief), E. J. Baron, M. A. Pfaller, F. C. Tenover and R. H. Yolken. ASM Press, Washington, D.C. seventh edition, 1999, 1773 p. In one embodiment, pharmaceutical compositions of the present invention are used for the prophylaxis or treatment of pharyngitis, erysipelas and impetigo, scarlet fever, and invasive diseases such as bacteremia and necrotizing fasciitis and also toxic shock. In one embodiment, pharmaceutical compositions of the invention are used for the treatment or prophylaxis of *Streptococcus* infection and/or diseases and symptoms mediated by *Streptococcus* infection, in particular group B *Streptococcus* (GBS or *S. agalactiae*), group A *Streptococcus* (*Streptococcus pyogenes*), *S. pneumoniae, S. dysgalactiae, S. uberis, S. nocardia* as well as *Staphylococcus aureus*. In a further embodiment, the *Streptococcus* infection is group B *Streptococcus* (GBS or *S. agalactiae*).

In a further embodiment, the invention provides a method for prophylaxis or treatment of *Streptococcus* infection in a host susceptible to *Streptococcus* infection comprising administering to said host a prophylactic or therapeutic amount of a composition of the invention.

In a further embodiment, the invention provides a method for prophylaxis or treatment of GBS infection in a host susceptible to GBS infection comprising administering to said host a prophylactic or therapeutic amount of a composition of the invention.

As used in the present application, the term "host" includes mammals. In a further embodiment, the mammal is a member of a dairy herd. In a further embodiment, the mammal is an expectant mother. In a further embodiment, the mammal is human. In a further embodiment, the host is a pregnant woman. In a further embodiment, the host is a nonpregnant adult. In a further embodiment, the host is a neonate or an infant.

In a particular embodiment, pharmaceutical compositions are administered to those hosts at risk of *Streptococcus* infection such as infants, elderly and immunocompromised hosts.

Pharmaceutical compositions are preferably in unit dosage form of about 0.001 to 100 μg/kg (antigen/body weight) and more preferably 0.01 to 10 μg/kg and most preferably 0.1 to 1 μg/kg 1 to 3 times with an interval of about 1 to 6 week intervals between immunizations.

Pharmaceutical compositions are preferably in unit dosage form of about 0.1 μg to 10 mg and more preferably 1 μg to 1 mg and most preferably 10 to 100 μg 1 to 3 times with an interval of about 1 to 6 week intervals between immunizations.

According to another aspect, there are provided polynucleotides encoding polypeptides characterized by the amino acid sequence comprising SEQ ID NO: 2 or fragments or analogs thereof.

In one embodiment, polynucleotides are those illustrated in SEQ ID No: 1 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridization can be readily determined by one of skilled in the art (see for example Sambrook et al., (1989) Molecular cloning: A Laboratory Manual, $2^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either (a) a DNA sequence encoding a polypeptide or (b) the complement of a DNA sequence encoding a polypeptide;

wherein said polypeptide comprises SEQ ID NO:2 or fragments or analogs thereof.

In a further embodiment, the present invention provides polynucleotides that hybridize under stringent conditions to either (a) a DNA sequence encoding a polypeptide or
(b) the complement of a DNA sequence encoding a polypeptide;
wherein said polypeptide comprises SEQ ID NO:2.

In a further embodiment, the present invention provides polynucleotides that hybridize under stringent conditions to either
(a) a DNA sequence encoding a polypeptide or
(b) the complement of a DNA sequence encoding a polypeptide;
wherein said polypeptide comprises at least 10 contiguous amino acid residues from a polypeptide comprising SEQ ID NO:2 or fragments or analogs thereof.

In a further embodiment, the present invention provides polynucleotides that hybridize under stringent conditions to either
(a) a DNA sequence encoding a polypeptide or
(b) the complement of a DNA sequence encoding a polypeptide;
wherein said polypeptide comprises at least 10 contiguous amino acid residues from a polypeptide comprising SEQ ID NO:2.

In a further embodiment, polynucleotides are those illustrated in SEQ ID NO: 1 encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product.

Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York.

The present invention provides a process for producing a polypeptide comprising culturing a host cell of the invention under conditions suitable for expression of said polypeptide.

For recombinant production, host cells are transfected with vectors which encode the polypeptides of the invention, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York). Suitable promoters include but are not limited to LTR or SV40 promoter, E. coli lac, tac or trp promoters and the phage lambda $P_L$ promoter. Vectors will preferably incorporate an origin of replication as well as selection markers i.e. ampicillin resistance gene. Suitable bacterial vectors include pET, pQE70, pQE60, pQE-9, pD10 phagescript, psi174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e. *E. coli, Bacillus subtilis, Streptomyces*; fungal i.e. *Aspergillus niger, Aspergillus nidulins*; yeast i.e. *Saccharomyces* or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptides may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397) or be chemically removed subsequent to purifying the expressed polypeptide.

According to a further aspect, the streptococcal polypeptides of the invention may be used in a diagnostic test for *Streptococcus* infection, in particular group B *Streptococcus* infection.

Several diagnostic methods are possible, for example detecting *Streptococcus* organism in a biological sample, the following procedure may be followed:
(a) obtaining a biological sample from a host;
(b) incubating an antibody or fragment thereof reactive with a *Streptococcus* polypeptide of the invention with the biological sample to form a mixture; and
(c) detecting specifically bound antibody or bound fragment in the mixture which indicates the presence of *Streptococcus*.

Alternatively, a method for the detection of antibody specific to a *Streptococcus* antigen in a biological sample containing or suspected of containing said antibody may be performed as follows:

(a) obtaining a biological sample from a host;

(b) incubating one or more *Streptococcus* polypeptides of the invention or fragments thereof with the biological sample to form a mixture; and (c) detecting specifically bound antigen or bound fragment in the mixture which indicates the presence of antibody specific to *Streptococcus*.

One of skill in the art will recognize that this diagnostic test may take several forms, including an immunological test such as an enzyme-linked immunosorbent assay (ELISA), a radio-immunoassay or a latex agglutination assay, essentially to determine whether antibodies specific for the protein are present in an organism.

The DNA sequences encoding polypeptides of the invention may also be used to design DNA probes for use in detecting the presence of *Streptococcus* in a biological sample suspected of containing such bacteria. The detection method of this invention comprises:

(a) obtaining the biological sample from a host;

(b) incubating one or more DNA probes having a DNA sequence encoding a polypeptide of the invention or fragments thereof with the biological sample to form a mixture; and (c) detecting specifically bound DNA probe in the mixture which indicates the presence of *Streptococcus* bacteria.

The DNA probes of this invention may also be used for detecting circulating *Streptococcus* i.e. group B *Streptococcus* nucleic acids in a sample, for example using a polymerase chain reaction, as a method of diagnosing *Streptococcus* infections. The probe may be synthesized using conventional techniques and may be immobilized on a solid phase, or may be labeled with a detectable label. A preferred DNA probe for this application is an oligomer having a sequence complementary to at least about 6 contiguous nucleotides of the group B *Streptococcus* polypeptides of the invention. In a further embodiment, the preferred DNA probe will be an oligomer having a sequence complementary to at least about 15 contiguous nucleotides of the group B *Streptococcus* polypeptides of the invention. In a further embodiment, the preferred DNA probe will be an oligomer having a sequence complementary to at least about 30 contiguous nucleotides of the group B *Streptococcus* polypeptides of the invention. In a further embodiment, the preferred DNA probe will be an oligomer having a sequence complementary to at least about 50 contiguous nucleotides of the group B *Streptococcus* polypeptides of the invention.

Another diagnostic method for the detection of *Streptococcus* in a host comprises:

(a) labeling an antibody reactive with a polypeptide of the invention or fragment thereof with a detectable label;

(b) administering the labeled antibody or labeled fragment to the host; and (c) detecting specifically bound labeled antibody or labeled fragment in the host which indicates the presence of *Streptococcus*.

A further aspect of the invention is the use of the *Streptococcus* polypeptides of the invention as immunogens for the production of specific antibodies for the diagnosis and in particular the treatment of *Streptococcus* infection. Suitable antibodies may be determined using appropriate screening methods, for example by measuring the ability of a particular antibody to passively protect against *Streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the Group B *Streptococcus* polypeptides but is preferably specific for one.

According to one aspect, the present invention provides the use of an antibody for treatment and/or prophylaxis of streptococcal infections.

A further aspect of the invention is the use of the antibodies directed to the polypeptides of the invention for passive immunization. One could use the antibodies described in the present application.

A further aspect of the invention is a method for immunization, whereby an antibody raised by a polypeptide of the invention is administered to a host in an amount sufficient to provide a passive immunization.

In a further embodiment, the invention provides the use of a pharmaceutical composition of the invention in the manufacture of a medicament for the prophylactic or therapeutic treatment of streptococcal infection.

In a further embodiment, the invention provides a kit comprising a polypeptide of the invention for detection or diagnosis of streptococcal infection.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

Example 1

This example illustrates the identification of Group B streptococcal BVH-A5 gene.

Chromosomal DNA was isolated from different Group B streptococcal strains as previously described (Jayarao, B M et al. 1991. *J. Clin. Microbiol.* 29:2774-2778). A λZAPExpress genomic library was constructed using chromosomal DNA purified from the serotype III Group B streptococcal strain NCS 954 (National Center for *Streptococcus*, Provincial Laboratory of Public Health for Northern Alberta, Edmonton, Canada) and screened according to the manufacturer's instructions (STRATAGENE, La Jolla, Calif.) with a pool of human normal sera. Briefly, the purified chromosomal DNA was partially digested with tsp509I restriction enzyme, and the resulting fragments were electrophoresed on a 1% agarose gel (BIO-RAD). Fragments in the 5- to 10-kb size range were extracted from the gel and ligated to the EcoRI arms of λZAPExpress vector and the vector was encapsidated using the Gigapack II packaging extract (STRATAGENE). The recombinant phages were used to infect *E. coli* XL1-Blue MRF' [Δ (mcrA) 183Δ (mcrCB-hsdSMR-mrr) 173 endA1 supE44 thi-1 recA1 gyrA96 relAI lac (F' proAB lac$^q$ZΔM15 Tn10 [Tet$^R$])], which was then plated onto LB agar. The resulting plaques were lifted onto HYBOND-C nitrocellulose membranes (Amersham Pharmacia Biotech, Baie d'Urfé, Québec, Canada) pre-impregnated with 10 mM Iso-propyl-β-d-thiogalactopyranoside (IPTG: ICN Biomedicals Inc., Costa Mesa, Calif.). The membranes were blocked using phosphate-buffered saline (PBS) with 3% skim milk and were sequentially incubated with the pooled of human sera, peroxidase-labeled goat anti-human immunoglobulins antisera (Jackson Immunoresearch Laboratories Inc., West Grove, Pa.) and substrate. Positive plaques were isolated and purified twice. The insert was amplified by PCR (DNA Thermal Cycler GeneAmp® PCR system 2400 Perkin Elmer, San Jose, Calif.) from positive phage DNA using the following oligonucleotide primers: T3pBK (5'-AATTAACCCTCAC-TAAAGGG-3') (SEQ ID NO: 11) and T7pBK (5'-GTAATACGACTCACTATAGGGC-3') (SEQ ID NO: 12). PCR product was purified from agarose gel using a QIA®quick gel extraction kit from QIA®gen (Chatsworth, Calif.) following the manufacturer's instructions. The sequence of the PCR product was determined using the TAQ Dye Deoxy Terminator Cycle Sequencing Kit with an Applied Biosystems Inc. (Foster City, Calif.) automated sequencer model 373A according to the manufacturer's recommendations. The sequence analysis revealed the presence of an ORF coding for a polypeptide with a signal peptide. This polypeptide was then identified as BVH-A5.

Example 2

This example illustrates the cloning of Group B streptococcal BVH-A5 gene.

The coding region of Group B streptococcal BVH-A5 (SEQ ID NO: 1) gene without the region coding for the leader peptide was amplified by PCR (DNA Thermal Cycler GeneAmp® PCR system 2400 Perkin Elmer) from genomic DNA of serotype III Group B streptococcal strain NCS 954 using oligonucleotide primers that contained base extensions for the addition of restriction sites NcoI (CCATGG) and XhoI (CTCGAG). The oligonucleotide primers (Table 1) DMAR577 and DMAR747 were used to amplify the BVH-A5 gene. PCR products were purified from agarose gel using a QIA®quick gel extraction kit from QIA®gen following the manufacturer's instructions, and digested with NcoI and XhoI (Amersham Pharmacia Biotech). The pET-21d (+) vector (NOVAGEN, Madison, Wis.) was digested with NcoI and XhoI and purified from agarose gel using a QIA®quick gel extraction kit from QIA®gen. The NcoI-XhoI PCR product was ligated to the NcoI-XhoI pET-21d (+) expression vector. The ligated product was transformed into *E. coli* strain STBL2 [F⁻ mcrA Δ(mcrBC-hsdRMS-mrr) recA1 endA1 lon gyrA96 thi-1 supE44 relA1 λ⁻ Δ(lac-proAB)] (GIBCO BRL, Gaithersburg, Md.) according to the manufacturer's recommendations. Recombinant pET-21d (+) plasmid (rpET21d (+)) containing BVH-A5 gene was purified using a QIA®gen plasmid kit and DNA insert was sequenced (Taq Dye Deoxy Terminator Cycle Sequencing kit, ABI, Foster City, Calif.).

It was determined that the open reading frame (ORF) which codes for BVH-A5 gene (SEQ ID NO: 1) contains 4740-bp and encodes a 1579 amino acid residues polypeptide with a predicted pI of 6.69 and a predicted molecular mass of 173,249.19 Da. Analysis of the predicted amino acid residues sequence (SEQ ID NO:2) using the Spscan software (Wisconsin Sequence Analysis Package; Genetics Computer Group) suggested the existence of a 43 amino acid residues signal peptide (MLQEKEIFMNTKQRFSIRKYKLGAVSV-LLGTLFFLGGITNVAA) (SEQ ID NO: 2, aa1-43), which ends with a cleavage site situated between an alanine and an aspartic acid residues. Analysis of the amino-acid-residues sequence revealed the presence of a cell attachment sequence (RGD) located between residues 454 and 456, and of a cell wall anchoring motif (LPXTG) located between residues 1544 and 1548. Comparison of the amino acid sequence of BVH-A5 (SEQ ID NO: 2) with the sequences compiled in the available databanks revealed 49% identity with the cell envelope proteinase of *Streptococcus thermophilus* (GeneBank accession number: AF243528: Fernandez-Espla, M D et al. 2000. *Appl. Environ. Microbiol.* 66: 4772-4778).

TABLE 1

Oligonucleotide primers used for PCR amplifications of Group B streptococcal BVH-A5 genes

| Genes | Primers I.D. | Restriction site | Vector | Sequence |
|---|---|---|---|---|
| BVH-A5 and BVH-A5-1 | DMAR577 | NcoI | pET21d | 5'-CATCCCATGGATTCTGTCATAAATAAGCCATCTG-3' (SEQ ID No: 3) |
| BVH-A5 and BVH-A5-3 | DMAR747 | XhoI | pET21d | 5'-GCAGCTCGAGTTCTCTTTTGATAGACTTTAGTTTGATTG-3' (SEQ ID No: 4) |
| BVH-A5 | DMAR748 | BamHI | pCMV-GH | 5'-ATCTGGATCCTGATTCTGTCATAAATAAGCCATCTG-3' (SEQ ID No.: 5) |
| BVH-A5 | DMAR749 | SalI | pCMV-GH | 5'-GCCGGTCGACTTATTCTCTTTTGATAGACTTTAGTTTG-3' (SEQ ID No: 6) |
| BVH-A5-1 | DMAR578a | XhoI | pET21d | 5'-CATCCTCGAGATCCTTTTCTTGTTTGATAAATAC-3' (SEQ ID No: 7) |

TABLE 1-continued

Oligonucleotide primers used for PCR amplifications of Group B streptococcal BVH-A5 genes

| Genes | Primers I.D. | Restriction site | Vector | Sequence |
|---|---|---|---|---|
| BVH-A5-2 | DMAR849 | NcoI | pET21d | 5'-CCGGCCATGGAAAACATTGATAGTAATAAAATTATC-3' (SEQ ID No: 8) |
| BVH-A5-2 | DMAR850 | XhoI | pET21d | 5'-TATACTCGAGTCTATTGGAAAGCAGCAATTCTGC-3' (SEQ ID No: 9) |
| BVH-A5-3 | DMAR851 | NcoI | pET21d | 5'-CATTCCATGGTAGAACACGGGGAATCTGGTATC-3' (SEQ ID No: 10) |

Example 3

This example describes the PCR amplification of Group B streptococcal BVH-A5 gene from other Group B strains.

To confirm the presence by PCR amplification of BVH-A5 (SEQ ID NO:1) gene, the following 11 serologically distinct Group B streptococcal strains were used: C388/90 (serotype Ia/c), ATCC12401 (serotype Ib), ATCC27591 (serotype Ic), NCS246 (serotype II/R), NCS954 (serotype III/R), NCS97SR331 (serotype IV), NCS535 (serotype V), NCS9842 (serotype VI), NCS7271 (serotype VII), NCS970886 (serotype VIII), and ATCC27956 (bovine isolate). These strains were obtained from the American Type Culture Collection (Rockville, Md., USA) and National Center for *Streptococcus*, Provincial Laboratory of Public Health for Northern Alberta (Edmonton, Alberta, Canada). The *E. coli* strain XL1-Blue MRF' was used in these experiments as negative control. Chromosomal DNA was isolated from each Group B streptococcal strain as previously described (Jayarao, B M et al. 1991. *J. Clin. Microbiol.* 29:2774-2778). BVH-A5 (SEQ ID NO:1) gene was amplified by PCR (DNA Thermal Cycler GeneAmp® PCR system 2400 Perkin Elmer) from the genomic DNA purified from the 11 Group B streptococcal strains, and the control *E. coli* strain using the following oligonucleotides presented in Table 1: DMAR577 and DMAR747. PCR was performed with 35 cycles of 30 sec at 94° C., 30 sec at 55° C. and 210 sec at 68° C. and a final elongation period of 10 min at 68° C. The PCR products were size fractionated in 1% agarose gels and were visualized by ethidium bromide staining. The results of these PCR amplifications are presented in Table 2. The analysis of the amplification products revealed that BVH-A5 (SEQ ID NO:1) gene was present in the genome of all of the 11 Group B streptococcal strains tested. No such product was detected when the control *E. coli* DNA was submitted to identical PCR amplifications with these oligonucleotide primers.

TABLE 2

Identification of BVH-A5 gene by PCR amplification in Group B streptococcal isolates.

| Strains identification | Presence of BVH-A5 gene |
|---|---|
| C388/90 (seriotype Ia/c) | + |
| ATCC12401 (serotype Ib) | + |
| ATCC27591 (serotype Ic) | + |
| NCS246 (serotype II/R) | + |
| NCS954 (serotype III/R) | + |
| NCS97SR331 (serotype IV) | + |
| NCS535 (serotype V) | + |
| NCS9842 (serotype VI) | + |
| NCS7271 (serotype VII) | + |
| NCS970886 (serotype VIII) | + |
| ATCC27956 (bovine isolate) | + |
| *E. coli* control strain XL1 Blue MRF' | − |

Example 4

This example illustrates the cloning of Group B streptococcal BVH-A5 gene in CMV plasmid pCMV-GH.

The DNA coding region of Group B streptococcal BHV-A5 (SEQ ID NO: 1) without the leader peptide was inserted in phase downstream of a human growth hormone (hGH) gene which was under the transcriptional control of the cytomegalovirus (CMV) promotor in the plasmid vector PCMV-GH (Tang et al., Nature, 1992, 356:152). The CMV promotor is non functional plasmid in *E. coli* cells but active upon administration of the plasmid in eukaryotic cells. The vector also incorporated the ampicillin resistance gene.

The coding region of BVH-A5 (SEQ ID NO: 1) gene without its leader peptide regions was amplified by PCR (DNA Thermal Cycler GeneAmp® PCR system 2400 Perkin Elmer) from genomic DNA of serotype III Group B streptococcal strain NCS 954 using oligonucleotide primers that contained base extensions for the addition of restriction sites BamHI (GGATCC) and SalI (GTCGAC). The oligonucleotide primers DMAR748 and DMAR749 were used to amplify the BVH-A5 (SEQ ID NO: 1) gene. The PCR product was purified from agarose gel using a QIA®quick gel extraction kit from QIA®gen and digested with restriction enzymes (AMERSHAM PHARMACIA Biotech). The PCMV-GH vector (Laboratory of Dr. Stephen A. Johnston, Department of Biochemistry, The University of Texas, Dallas, Tex.) was digested with BamHI and SalI and purified from agarose gel using the QIA®quick gel extraction kit from QIA®gen. The BamHI-SalI DNA fragments were ligated to the BamHI-SalI PCMV-GH vector to create the hGH-BVH-A5 fusion protein under the control of the CMV promoter. The ligated product was transformed into *E. coli* strain DH5α [φ80dlacZΔM15 Δ(lacZYA-argF) U169 endA1 recA1 hsdR17 ($r_K^-$–$m_K^-$+) deoR thi-1 supE44 λ$^-$gyrA96 relA1] (GIBCO BRL) according to the method of Simanis (Hanahan, D. DNA Cloning, 1985, D. M. Glover (ed), pp. 109-135). The recombinant pCMV plasmid was purified using a QIA®gen plasmid kit and the nucleotide sequence of the DNA insert was verified by DNA sequencing.

Example 5

This example illustrates the use of DNA to elicit an immune response to Group B streptococcal BVH-A5 polypeptide antigen.

Groups of 8 female BALB/c mice (Charles River, St-Constant, Québec, Canada) are immunized by intramuscular injection of 100 µl three times at two- or three-week intervals with 50 µg of recombinant PCMV-GH encoding BVH-A5 (SEQ ID NO: 1) gene in presence of 50 µg of granulocyte-macrophage colony-stimulating factor (GM-CSF)—expressing plasmid pCMV-GH-GM-CSF (Laboratory of Dr. Stephen A. Johnston, Department of Biochemistry, The University of Texas, Dallas, Tex.). As control, groups of mice are injected with 50 µg of PCMV-GH in presence of 50 µg of pCMV-GH-GM-CSF. Blood samples are collected from the orbital sinus prior to each immunization and seven days following the third injection and serum antibody responses are determined by ELISA using purified BVH-A5-His·Tag recombinant polypeptides as coating antigen.

Example 6

This example illustrates the production and purification of recombinant Group B streptococcal BVH-A5 polypeptide.

The recombinant pET-21d (+) plasmid with BVH-A5 gene corresponding to the SEQ ID NO: 1 was used to transform by electroporation (Gene Pulser II apparatus, BIO-RAD Labs, Mississauga, Ontario, Canada) *E. coli* strain BL21 (DE3) (F$^-$ompT hsdS$_B$ ($r^-_B m^-_B$) gal dcm (DE3)) (NOVAGEN, Madison, Wis.). In this strain of *E. coli*, the T7 promoter controlling expression of the recombinant polypeptide is specifically recognized by the T7 RNA polymerase (present on the λDE3 prophage) whose gene is under the control of the lac promoter which is inducible by IPTG. The transformants BL21 (DE3)/rpET21 were grown at 37° C. with agitation at 250 rpm in LB broth (peptone 10 g/L, yeast extract 5 g/L, NaIl 10 g/L) containing 100 µg of carbenicillin (SIGMA-ALDRICH Canada Ltd., Oakville, Ontario, Canada) per ml until the $A_{600}$ reached a value of 0.6. In order to induce the production of Group B streptococcal BVH-A5-His·Tag recombinant polypeptide, the cells were incubated for 3 additional hours in the presence of IPTG at a final concentration of 1 mM. Induced cells from a 500 ml culture were pelleted by centrifugation and frozen at −70° C.

The purification of the recombinant polypeptides from the soluble cytoplasmic fraction of IPTG-induced BL21 (DE3)/rpET2ld (+) was done by affinity chromatography based on the properties of the His·Tag sequence (6 consecutive histidine residues) to bind to divalent cations (Ni$^{2+}$) immobilized on the His·Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 1 mM PMSF, sonicated and centrifuged at 12,000×g for 20 min to remove debris. The supernatant was deposited on a Ni-NTA agarose column (QIA®gen). The Group B streptococcal BVH-A5-His·Tag recombinant polypeptide was eluted with 250 mM imidazole-500 mM NaCl-20 mM Tris pH 7.9. The removal of the salt and imidazole from the samples was done by dialysis against PBS at 4° C. The quantities of recombinant polypeptides obtained from the soluble fraction of *E. coli* was estimated by MicroBCA® (Pierce, Rockford, Ill.).

Example 7

This example illustrates the reactivity of the BVH-A5 His-tagged GBS recombinant polypeptide with human sera and sera collected from mice after immunization with a GBS antigenic preparation.

As shown in Table 3, BVH-A5 His-tagged recombinant polypeptide was recognized in immunoblots by the antibodies present in the pool of normal human sera. This is an important result since it clearly indicates that humans which are normally in contact with GBS do develop antibodies that are specific to that polypeptide. These particular human antibodies might be implicated in the protection against GBS infection. In addition, immunoblots also revealed that sera collected from mice immunized with a GBS antigenic preparation enriched outer surface polypeptides which induced significant protection in a mouse model also developed antibodies that recognized BVH-A5 His-tagged recombinant polypeptide. These results indicate that this polypeptide was present in GBS antigenic preparation that protected mice against infection and that it induced antibodies that reacted with the corresponding BVH-A5 His-tagged recombinant polypeptide.

TABLE 3

Reactivity in immunoblots of antibodies present in human sera and sera collected from mice after immunization with a GBS antigenic preparation with BVH-A5 His-tagged fusion recombinant polypeptide.

| Purified recombinant polypeptide I.D.[1] | Reactivity in immunoblots with | |
|---|---|---|
| | Human sera[2] | Mouse sera[3] |
| BVH-A5 | + | + |

[1]His-tagged recombinant polypeptide produced and purified as described in Example 6 was used to perform the immunoblots.
[2]Sera collected from human were pooled together and diluted 1/500 to perform the immunoblots.
[3]Mouse sera collected after immunization with a GBS antigenic preparation enriched outer surface proteins were pooled and diluted 1/500 to perform the immunoblots. These mice were protected against a lethal GBS challenge.

Example 8

This example describes the cloning of truncated BVH-A5 gene products by polymerase chain reaction (PCR) and the expression of truncated BVH-A5 molecules.

Gene fragments were amplified by PCR (DNA Thermal Cycler GeneAmp® PCR system 2400 Perkin Elmer) from genomic DNA of serotype III Group B streptococcal strain NCS 954 using oligonucleotide primers presented in Table 1. The methods used for cloning the truncated BVH-A5 gene products into an expression vector and sequencing are similar to the methods described in Example 2. The recombinant polypeptides were purified from supernatant fractions obtained after centrifugation of sonicated IPTG-induced *E. coli* cultures using a His-Bind metal chelation resin (QIA®gen) as described in Example 6. The gene products generated are listed in the Table 4.

TABLE 4

Lists of truncated BVH-A5 gene products generated from serotype III Group B streptococcal strain NCS 954.

| PCR-primer sets | Polypeptide designation | Identification on SEQ ID No: 2 | Cloning vector |
|---|---|---|---|
| DMAR577-DMAR578a | BVH-A5-1 | 43 aa to 1045 aa | pET21d |
| DMAR849-DMAR850 | BVH-A5-2 | 152 aa to 1453 aa | pET21d |
| DMAR851-DMAR747 | BVH-A5-3 | 996 aa to 1579 aa | pET21d |

Example 9

This example illustrates the protection of mice against fatal Group B streptococcal infection induced by immunization with recombinant truncated BVH-A5 polypeptides.

Groups of female CD-1 mice (Charles River) were immunized subcutaneously three times at two-week intervals with 20 μg of truncated BVH-A5-1-His·Tag polypeptides in presence of 10 μg of Quil™ A adjuvant (Cedarlane Laboratories Ltd, Hornby, Ontario, Canada). The control mice were injected with QuilA™ adjuvant alone in PBS. Blood samples were collected from the orbital sinus on day 1, 14, and 28 prior to each immunization and 14 days (day 42) following the third injection. One week later the mice were challenged with a lethal dose of the GBS strains. Samples of the Group B streptococcal challenge inoculum were plated on blood agar plates to determine the CFU and to verify the challenge dose. Deaths were recorded for a period of 7 days. The survival data are presented in Table 5. More than 74% of the mice immunized with either BVH-A5-1 and BVH-A5-2 recombinant polypeptides were protected against a challenge with the GBS strain C388/90 (Ia/c). Similar protection was obtained against a lethal challenge with the strains NCS 251 (II) and NCS 535 (V). On the contrary, the immunization of mice with BVH-A5-3 did not confer such protection against challenge with GBS strain C388/90 (I a/c). The survival rate determined for the groups immunized with BVH-A5-1 and BVH-A5-2 were shown to be statistically different from the control group by Fisher's exact test.

TABLE 5

Survival of CD-1 mice immunized with purified recombinant truncated BVH-A5 polypeptides.

| Strains used for challenge (serotype) | Groups | Number of mice surviving the GBS challenge/total (%)[1] | p[2] |
|---|---|---|---|
| C388/90 (I a/c) | BVH-A5-1 | 52/64 (81) | <0.0001 |
| | Control | 12/64 (19) | |
| | BVH-A5-2 | 17/23 (74) | <0.0002 |
| | Control | 5/24 (21) | |
| | BVH-A5-3 | 7/15 (47) | 0.1597 |
| | Control | 4/16 (25) | |
| NCS 251 (II) | BVH-A5-1 | 6/8 (75) | <0.0500 |
| | Control | 2/8 (25) | |
| NCS 535 (V) | BVH-A5-1 | 7/8 (88) | 0.0079 |
| | Control | 2/8 (25) | |

[1] Number of survivors was evaluated for 7 days after challenge. The mice were immunized subcutaneously three times with 20 μg of purified recombinant polypeptides or adjuvant only. After immunization, the mice were challenged intraperitoneally with a lethal dose of a GBS strain.
[2] Fisher's exact test was determined against control group.

The invention claimed is:

1. An isolated polypeptide comprising a polypeptide fragment, wherein the polypeptide fragment comprises at least 15 contiguous amino acids of a polypeptide consisting of the amino acid sequence set forth in SEQ ID NO:2, wherein the polypeptide fragment is capable of eliciting antibodies that specifically bind to the polypeptide consisting of the amino acid sequence set forth in SEQ ID NO:2.

2. The isolated polypeptide according to claim 1, wherein the polypeptide fragment comprises at least 15 contiguous amino acids of a polypeptide consisting of the amino acid sequence set forth at positions 43-1045 of SEQ ID NO:2.

3. A chimeric polypeptide comprising (a) two or more polypeptide fragments, wherein the two or more polypeptide fragments each comprise at least 15 contiguous amino acids of a polypeptide consisting of the amino acid sequence set forth in SEQ ID NO: 2; provided that the two or more polypeptide fragments are linked to form a chimeric polypeptide, wherein the two or more polypeptide fragments are capable of eliciting antibodies that specifically bind to the polypeptide consisting of the amino acid sequence set forth in SEQ ID NO:2.

4. A pharmaceutical composition comprising the isolated polypeptide according to claim 1 or claim 2 and a pharmaceutically acceptable carrier, diluent or adjuvant.

5. A method for inducing an immune response in a host comprising administering to said host the composition according to claim 4.

6. Kit comprising the isolated polypeptide according to claim 1 for detection or diagnosis of a group B streptococcus infection.

7. The isolated polypeptide according to claim 1 or claim 2 wherein the isolated polypeptide is coupled or conjugated to a carrier protein.

8. A pharmaceutical composition comprising the isolated polypeptide according to claim 7 and a pharmaceutically acceptable carrier, diluent or adjuvant.

9. The chimeric polypeptide according to claim 3 wherein the two or more polypeptide fragments each comprise at least 15 contiguous amino acids of a polypeptide consisting of the amino acid sequence set forth at positions 43-1045 of SEQ ID NO:2.

10. The chimeric polypeptide according to claim 3 or claim 9 wherein the chimeric polypeptide is coupled or conjugated to a carrier protein.

11. A pharmaceutical composition comprising the chimeric polypeptide according to claim 3 or claim 9 and a pharmaceutically acceptable carrier, diluent or adjuvant.

12. A pharmaceutical composition comprising the chimeric polypeptide according to claim 10 and a pharmaceutically acceptable carrier, diluent or adjuvant.

* * * * *

SEQUENCE LISTING

<160> NUMBER OF SEQ ID NOS: 12

<210> SEQ ID NO 1
<211> LENGTH: 4740
<212> TYPE: DNA
<213> ORGANISM: Group B streptococcus strain NCS 954

<400> SEQUENCE: 1

```
atgttacaag aaaaggagat ttttatgaac acaaaacagc gtttttcaat ccggaaatat      60
aagttaggtg ccgtatctgt acttttggga accctatttt ttttaggcgg tatcacaaat     120
gtagctgctg attctgtcat aaataagcca tctgatattg cagttgaaca gcaagtaaaa     180
gacagtccaa cgagcatagc aaatgagaca cctactaaca cacgtcatc agcccttgcg      240 tcaacagctc aagacaatct tgttacaaag gctaataata atagtccaac agaaacacaa     300
ccagtaactg agcctcactc tcaagccacc gagacatttt ccccagccgc aaatcaaccg     360
gttgaaagca ctcaagaagt ttctaaaact cctttaacca aacaaaattt agcagtcaaa     420
cctacaccag ctatttctaa agaaccccct caaaacattg atagtaataa aattatcact     480
gtccccaaag tatggaacac aggctacaaa ggagagggaa ctgttgtagc aattattgac     540
tcaggactag ataccaatca cgatgctctc caattaaatg attcgacaaa agcaaaatac     600
caaaacgaac agcaaatgaa tgctgctaaa gcaaaagctg tataaaacta tggaaaatgg     660
tataacaaca aagtaatctt tggtcacaac tatgttgatg tcaatacaga gctaaaagag     720 gtgaaagca cttctcatgg tatgcacgta accagtatcg caacagctaa tcctagcaag     780
aaagatacaa atgaattaat ctatggtgtt gctcctgaag cacaagtaat gtttatgaga     840
```

-continued

```
gtcttctctg atgaaaaaag aggaactgga ccagcccttt atgttaaagc tattgaagat    900
gccgttaaac tcggtgctga tagcattaat ttaagtttag gtggagctaa tggctcttta    960
gttaatgccg atgaccgact tataaaagct ttagagatgg ctagactcgc tggcgtttct   1020
gttgttatag cagcaggtaa cgacggtaca tttgggagtg gagcatcaaa gccttctgct   1080
ctttatcctg attatggttt agttggtagt ccatcaacag ctcgtgaggc catttctgta   1140
gcatcatata ataatacaac actggttaat aaagtcttca acattatcgg attagaaaac   1200
aacaaaaatc tcaacaacgg attagctgct tatgcagatc ctaaagttag tgataagacc   1260
tttgaagtag ggaagcaata tgattatgtt ttcgtaggaa aaggaaacga caatgattat   1320
aaggacaaaa ctttaaatgg taaaatcgcc ttaattgaac gtggagatat tacttttaca   1380
aaaaaagtcg tcaacgctat taatcacggt gctgtgggag ctattatctt taataacaaa   1440
gctggagaag ctaatctaac aatgagttta gatcctgaag caagcgctat tcctgccatt   1500
tttactcaaa aagagtttgg agatgtttta gctaaaaaca actataaaat tgtatttaac   1560
aatatcaaaa ataaacaagc caaccctaat gcaggtgtcc tatctgactt ttcaagctgg   1620
ggattaacag cagacggaca attaaaacct gacttatctg ctcctggagg ctctatttac   1680
gccgctatca atgataatga atatgatatg atgagtggga caagtatggc ttctccccat   1740
gtcgctggtg ctactgctct agttaaacaa tacttattga agaacatcc agaacttaaa   1800
aaaggtgaca ttgaaagaac tgtcaaatac cttcttatga gtactgctaa agcacaccta   1860
aacaaagata caggcgctta cacctcacca cgccaacaag gagcaggtat tatcgatgtc   1920
gcagcagcag ttcagacagg attataccta actggtgggg aaaacaacta tggtagcgtt   1980
acattaggaa atattaaaga taaaatttcc tttgatgtta ctgttcataa tatcaataaa   2040
gttgcaaaag atttacacta tacaacctat ttaaatactg atcaagttaa agatggcttt   2100
gtcacattag ctcctcaaca acttggtaca tttacaggga aaacgatacg gattgaacca   2160
gggcaaacta aaacgattac aattgatata gatgtttcga ataccatga catgttaaaa   2220
aaagtaatgc caaacggcta tttcctagaa ggctacgtac gttttacaga ccctgttgat   2280
ggtggggaag ttcttagtat tccttatgtt ggatttaagg gagaattcca aaacttagaa   2340
gttttagaaa aatccattta taagcttgtt gctaacaaag aaaagggatt ttatttccaa   2400
ccgaaacaaa caaacgaagt tcctggttca gaagattata ctgccttaat gactacaagt   2460
tcagagccta tctactcaac agacggtact agtcctatcc aattgaaagc ttgggaagc   2520
tataagtcta tagatggaaa atggatctta caactagagc aaaaaggcca gcctcatcta   2580
gccatttcac ctaatgatga ccaaaatcaa gatgccgttg cactgaaagg tgttttctta   2640
cgtaatttca ataatttaag agccaaagtc tatcgtgcag atgatgttaa tttacaaaaa   2700
ccactatggg taagtgctcc ccaagcagga gataaaatt actacagcgg aaatactgaa   2760
aatccaaaat ctacatttt tatgacaca gaatggaaag gaaccactac tgatggtatt   2820
cctttagaag atggaaaata caaatacgtt ttaacatact actctgatgt ccctggctct   2880
aagccacaac aaatggtatt tgatatcact ttggatagac aagctcctac actaacaaca   2940
gcaacttatg acaaagatag acgtatcttc aaagctcgtc ctgcagtaga acacggggaa   3000
tctggtatct ttagagaaca gttttttac ttaaaaaaag ataaagatgg tcattataat   3060
agcgtcttac gtcaaaaagg agaagacggt atccttgttg aagataacaa agtatttatc   3120
aaacaagaaa aggatggtag ctttattcta cctaagagg ttaatgattt ctctcatgtc   3180
```

-continued

```
tactacactg ttgaagatta tgcaggcaat ctagtgtcag caaaactcga agatttgatc    3240
aatattggca ataaaaatgg tttagtaaac gtcaaagtgt ttagccctga gcttaacagt    3300
aatgtcgata ttgatttctc ttactctgtc aaagatgaca aaggtaatgt catcaaaaag    3360
caacatcacg ggaaagacct caatttactg aaattgcctt ttggtaccta tacgtttgac    3420
ctattcttat acgatgagga acgagcaaat ctaatcagtc cccaaagtgt cactgtaact    3480
atttctgaaa aagatagcct taaagacgtc ttatttaaag ttaacttact caagaaagca    3540
gccttactcg ttgaatttga caagctttta ccaaaggag caacagtcca gttggttact    3600
aagacaaata ctgttgttga tctaccaaaa gcaacttatt ctcctactga ctatggtaaa    3660
aacatacctg taggagacta tcgtttaaac gtaacgctgc ctagtgggta tagcactta    3720 gagaacttag atgatttact tgtatccgta aagaaggtc aagtaaatct aacaaaattg    3780
acgctgatta ataaagctcc tctaattaat gccctagcag aacaaactga cattatttcc    3840
caacctgtgt tttataatgc tggaactcac ttaaaaaata attacctagc taatcttgaa    3900
aaggcacaaa cttaattaa aaatagagtg gaacaaacaa gtattgataa tgctattgct    3960
gctttgagag aaagtcgcca agctcttaac ggtaaagaaa cagatacttc tttactggca    4020
aaagctattt tagctgaaac agaaatcaag ggaaactatc aatttgttaa tgctagtcca    4080
ttaagccaat caactatat caatcaagtc caattggcga aaatcttct acaaaaacct    4140 aacgtcactc aatcagaagt agacaaagcc ttagaaaatc ttgatattgc taaaaatcaa    4200
ttaaatggtc atgaaactga ttactctggt ttacaccata tgataattaa agcaaatgtt    4260
ctgaaacaaa catcatctaa atatcagaac gccagtcaat ttgctaaaga aaattataat    4320
aaccttatca agaaagcaga attgctgctt tccaatagac aagctacaca agctcaagtt    4380
gaagagttat taaaccaaat aaaagcaacc gaacaagaac ttgatggtcg cgatagagtt    4440
tcttccgcag agaattatag tcaatcactc aatgataatg actctctcaa taccacacct    4500
atcaatccgc caaatcagcc ccaggcgttg atattcaaaa aaggcatgac taaagaaagt    4560
gaggttgctc agaagcgtgt cttagggttg actagccaaa ccgataatca aaagataaag    4620
acaaacaagc ttcctaaaac aggcgaaagc actcctaaaa taacctatac aatattgcta    4680
tttagtctct ctatgctagg tctggcaaca atcaaactaa agtctatcaa aagagaataa    4740
```

<210> SEQ ID NO 2
<211> LENGTH: 1579
<212> TYPE: PRT
<213> ORGANISM: Group B streptococcus strain NCS 954

<400> SEQUENCE: 2

```
Met Leu Gln Glu Lys Glu Ile Phe Met Asn Thr Lys Gln Arg Phe Ser
1               5                   10                  15

Ile Arg Lys Tyr Lys Leu Gly Ala Val Ser Val Leu Leu Gly Thr Leu
            20                  25                  30

Phe Phe Leu Gly Gly Ile Thr Asn Val Ala Ala Asp Ser Val Ile Asn
        35                  40                  45

Lys Pro Ser Asp Ile Ala Val Glu Gln Gln Val Lys Asp Ser Pro Thr
    50                  55                  60

Ser Ile Ala Asn Glu Thr Pro Thr Asn Asn Thr Ser Ser Ala Leu Ala
65                  70                  75                  80

Ser Thr Ala Gln Asp Asn Leu Val Thr Lys Ala Asn Asn Asn Ser Pro
                85                  90                  95

Thr Glu Thr Gln Pro Val Thr Glu Pro His Ser Gln Ala Thr Glu Thr
```

-continued

```
            100                 105                 110
Phe Ser Pro Ala Ala Asn Gln Pro Val Glu Ser Thr Gln Glu Val Ser
        115                 120                 125
Lys Thr Pro Leu Thr Lys Gln Asn Leu Ala Val Lys Pro Thr Pro Ala
        130                 135                 140
Ile Ser Lys Glu Thr Pro Gln Asn Ile Asp Ser Asn Lys Ile Ile Thr
145                 150                 155                 160
Val Pro Lys Val Trp Asn Thr Gly Tyr Lys Gly Glu Gly Thr Val Val
                165                 170                 175
Ala Ile Ile Asp Ser Gly Leu Asp Thr Asn His Asp Ala Leu Gln Leu
                180                 185                 190
Asn Asp Ser Thr Lys Ala Lys Tyr Gln Asn Glu Gln Gln Met Asn Ala
            195                 200                 205
Ala Lys Ala Lys Ala Gly Ile Asn Tyr Gly Lys Trp Tyr Asn Asn Lys
        210                 215                 220
Val Ile Phe Gly His Asn Tyr Val Asp Val Asn Thr Glu Leu Lys Glu
225                 230                 235                 240
Val Lys Ser Thr Ser His Gly Met His Val Thr Ser Ile Ala Thr Ala
                245                 250                 255
Asn Pro Ser Lys Lys Asp Thr Asn Glu Leu Ile Tyr Gly Val Ala Pro
            260                 265                 270
Glu Ala Gln Val Met Phe Met Arg Val Phe Ser Asp Glu Lys Arg Gly
        275                 280                 285
Thr Gly Pro Ala Leu Tyr Val Lys Ala Ile Glu Asp Ala Val Lys Leu
        290                 295                 300
Gly Ala Asp Ser Ile Asn Leu Ser Leu Gly Gly Ala Asn Gly Ser Leu
305                 310                 315                 320
Val Asn Ala Asp Asp Arg Leu Ile Lys Ala Leu Glu Met Ala Arg Leu
                325                 330                 335
Ala Gly Val Ser Val Val Ile Ala Ala Gly Asn Asp Gly Thr Phe Gly
            340                 345                 350
Ser Gly Ala Ser Lys Pro Ser Ala Leu Tyr Pro Asp Tyr Gly Leu Val
        355                 360                 365
Gly Ser Pro Ser Thr Ala Arg Glu Ala Ile Ser Val Ala Ser Tyr Asn
    370                 375                 380
Asn Thr Thr Leu Val Asn Lys Val Phe Asn Ile Ile Gly Leu Glu Asn
385                 390                 395                 400
Asn Lys Asn Leu Asn Asn Gly Leu Ala Ala Tyr Ala Asp Pro Lys Val
                405                 410                 415
Ser Asp Lys Thr Phe Glu Val Gly Lys Gln Tyr Asp Tyr Val Phe Val
            420                 425                 430
Gly Lys Gly Asn Asp Asn Asp Tyr Lys Asp Lys Thr Leu Asn Gly Lys
        435                 440                 445
Ile Ala Leu Ile Glu Arg Gly Asp Ile Thr Phe Thr Lys Lys Val Val
        450                 455                 460
Asn Ala Ile Asn His Gly Ala Val Gly Ala Ile Ile Phe Asn Asn Lys
465                 470                 475                 480
Ala Gly Glu Ala Asn Leu Thr Met Ser Leu Asp Pro Glu Ala Ser Ala
                485                 490                 495
Ile Pro Ala Ile Phe Thr Gln Lys Glu Phe Gly Asp Val Leu Ala Lys
            500                 505                 510
Asn Asn Tyr Lys Ile Val Phe Asn Asn Ile Lys Asn Lys Gln Ala Asn
        515                 520                 525
```

```
Pro Asn Ala Gly Val Leu Ser Asp Phe Ser Ser Trp Gly Leu Thr Ala
    530                 535                 540
Asp Gly Gln Leu Lys Pro Asp Leu Ser Ala Pro Gly Gly Ser Ile Tyr
545                 550                 555                 560
Ala Ala Ile Asn Asp Asn Glu Tyr Asp Met Met Ser Gly Thr Ser Met
                565                 570                 575
Ala Ser Pro His Val Ala Gly Ala Thr Ala Leu Val Lys Gln Tyr Leu
            580                 585                 590
Leu Lys Glu His Pro Glu Leu Lys Lys Gly Asp Ile Glu Arg Thr Val
        595                 600                 605
Lys Tyr Leu Leu Met Ser Thr Ala Lys Ala His Leu Asn Lys Asp Thr
    610                 615                 620
Gly Ala Tyr Thr Ser Pro Arg Gln Gln Gly Ala Gly Ile Ile Asp Val
625                 630                 635                 640
Ala Ala Ala Val Gln Thr Gly Leu Tyr Leu Thr Gly Gly Glu Asn Asn
                645                 650                 655
Tyr Gly Ser Val Thr Leu Gly Asn Ile Lys Asp Lys Ile Ser Phe Asp
            660                 665                 670
Val Thr Val His Asn Ile Asn Lys Val Ala Lys Asp Leu His Tyr Thr
        675                 680                 685
Thr Tyr Leu Asn Thr Asp Gln Val Lys Asp Gly Phe Val Thr Leu Ala
    690                 695                 700
Pro Gln Gln Leu Gly Thr Phe Thr Gly Lys Thr Ile Arg Ile Glu Pro
705                 710                 715                 720
Gly Gln Thr Lys Thr Ile Thr Ile Asp Ile Asp Val Ser Lys Tyr His
                725                 730                 735
Asp Met Leu Lys Lys Val Met Pro Asn Gly Tyr Phe Leu Glu Gly Tyr
            740                 745                 750
Val Arg Phe Thr Asp Pro Val Asp Gly Gly Glu Val Leu Ser Ile Pro
        755                 760                 765
Tyr Val Gly Phe Lys Gly Glu Phe Gln Asn Leu Glu Val Leu Glu Lys
    770                 775                 780
Ser Ile Tyr Lys Leu Val Ala Asn Lys Glu Lys Gly Phe Tyr Phe Gln
785                 790                 795                 800
Pro Lys Gln Thr Asn Glu Val Pro Gly Ser Glu Asp Tyr Thr Ala Leu
                805                 810                 815
Met Thr Thr Ser Ser Glu Pro Ile Tyr Ser Thr Asp Gly Thr Ser Pro
            820                 825                 830
Ile Gln Leu Lys Ala Leu Gly Ser Tyr Lys Ser Ile Asp Gly Lys Trp
        835                 840                 845
Ile Leu Gln Leu Glu Gln Lys Gly Gln Pro His Leu Ala Ile Ser Pro
    850                 855                 860
Asn Asp Asp Gln Asn Gln Asp Ala Val Ala Leu Lys Gly Val Phe Leu
865                 870                 875                 880
Arg Asn Phe Asn Asn Leu Arg Ala Lys Val Tyr Arg Ala Asp Asp Val
                885                 890                 895
Asn Leu Gln Lys Pro Leu Trp Val Ser Ala Pro Gln Ala Gly Asp Lys
            900                 905                 910
Asn Tyr Tyr Ser Gly Asn Thr Glu Asn Pro Lys Ser Thr Phe Leu Tyr
        915                 920                 925
Asp Thr Glu Trp Lys Gly Thr Thr Asp Gly Ile Pro Leu Glu Asp
    930                 935                 940
```

-continued

Gly Lys Tyr Lys Tyr Val Leu Thr Tyr Tyr Ser Asp Val Pro Gly Ser
945                 950                 955                 960

Lys Pro Gln Gln Met Val Phe Asp Ile Thr Leu Asp Arg Gln Ala Pro
                965                 970                 975

Thr Leu Thr Thr Ala Thr Tyr Asp Lys Asp Arg Arg Ile Phe Lys Ala
        980                 985                 990

Arg Pro Ala Val Glu His Gly Glu Ser Gly Ile Phe Arg Glu Gln Val
        995                 1000                1005

Phe Tyr Leu Lys Lys Asp Lys Asp Gly His Tyr Asn Ser Val Leu
    1010                1015                1020

Arg Gln Lys Gly Glu Asp Gly Ile Leu Val Glu Asp Asn Lys Val
    1025                1030                1035

Phe Ile Lys Gln Glu Lys Asp Gly Ser Phe Ile Leu Pro Lys Glu
    1040                1045                1050

Val Asn Asp Phe Ser His Val Tyr Tyr Thr Val Glu Asp Tyr Ala
    1055                1060                1065

Gly Asn Leu Val Ser Ala Lys Leu Glu Asp Leu Ile Asn Ile Gly
    1070                1075                1080

Asn Lys Asn Gly Leu Val Asn Val Lys Val Phe Ser Pro Glu Leu
    1085                1090                1095

Asn Ser Asn Val Asp Ile Asp Phe Ser Tyr Ser Val Lys Asp Asp
    1100                1105                1110

Lys Gly Asn Val Ile Lys Lys Gln His His Gly Lys Asp Leu Asn
    1115                1120                1125

Leu Leu Lys Leu Pro Phe Gly Thr Tyr Thr Phe Asp Leu Phe Leu
    1130                1135                1140

Tyr Asp Glu Glu Arg Ala Asn Leu Ile Ser Pro Gln Ser Val Thr
    1145                1150                1155

Val Thr Ile Ser Glu Lys Asp Ser Leu Lys Asp Val Leu Phe Lys
    1160                1165                1170

Val Asn Leu Leu Lys Lys Ala Ala Leu Leu Val Glu Phe Asp Lys
    1175                1180                1185

Leu Leu Pro Lys Gly Ala Thr Val Gln Leu Val Thr Lys Thr Asn
    1190                1195                1200

Thr Val Val Asp Leu Pro Lys Ala Thr Tyr Ser Pro Thr Asp Tyr
    1205                1210                1215

Gly Lys Asn Ile Pro Val Gly Asp Tyr Arg Leu Asn Val Thr Leu
    1220                1225                1230

Pro Ser Gly Tyr Ser Thr Leu Glu Asn Leu Asp Asp Leu Leu Val
    1235                1240                1245

Ser Val Lys Glu Gly Gln Val Asn Leu Thr Lys Leu Thr Leu Ile
    1250                1255                1260

Asn Lys Ala Pro Leu Ile Asn Ala Leu Ala Glu Gln Thr Asp Ile
    1265                1270                1275

Ile Ser Gln Pro Val Phe Tyr Asn Ala Gly Thr His Leu Lys Asn
    1280                1285                1290

Asn Tyr Leu Ala Asn Leu Glu Lys Ala Gln Thr Leu Ile Lys Asn
    1295                1300                1305

Arg Val Glu Gln Thr Ser Ile Asp Asn Ala Ile Ala Ala Leu Arg
    1310                1315                1320

Glu Ser Arg Gln Ala Leu Asn Gly Lys Glu Thr Asp Thr Ser Leu
    1325                1330                1335

Leu Ala Lys Ala Ile Leu Ala Glu Thr Glu Ile Lys Gly Asn Tyr

-continued

```
                1340                1345                1350

Gln Phe Val Asn Ala Ser Pro Leu Ser Gln Ser Thr Tyr Ile Asn
    1355                1360                1365

Gln Val Gln Leu Ala Lys Asn Leu Leu Gln Lys Pro Asn Val Thr
    1370                1375                1380

Gln Ser Glu Val Asp Lys Ala Leu Glu Asn Leu Asp Ile Ala Lys
    1385                1390                1395

Asn Gln Leu Asn Gly His Glu Thr Asp Tyr Ser Gly Leu His His
    1400                1405                1410

Met Ile Ile Lys Ala Asn Val Leu Lys Gln Thr Ser Ser Lys Tyr
    1415                1420                1425

Gln Asn Ala Ser Gln Phe Ala Lys Glu Asn Tyr Asn Asn Leu Ile
    1430                1435                1440

Lys Lys Ala Glu Leu Leu Leu Ser Asn Arg Gln Ala Thr Gln Ala
    1445                1450                1455

Gln Val Glu Glu Leu Leu Asn Gln Ile Lys Ala Thr Glu Gln Glu
    1460                1465                1470

Leu Asp Gly Arg Asp Arg Val Ser Ser Ala Glu Asn Tyr Ser Gln
    1475                1480                1485

Ser Leu Asn Asp Asn Asp Ser Leu Asn Thr Thr Pro Ile Asn Pro
    1490                1495                1500

Pro Asn Gln Pro Gln Ala Leu Ile Phe Lys Lys Gly Met Thr Lys
    1505                1510                1515

Glu Ser Glu Val Ala Gln Lys Arg Val Leu Gly Val Thr Ser Gln
    1520                1525                1530

Thr Asp Asn Gln Lys Ile Lys Thr Asn Lys Leu Pro Lys Thr Gly
    1535                1540                1545

Glu Ser Thr Pro Lys Ile Thr Tyr Thr Ile Leu Leu Phe Ser Leu
    1550                1555                1560

Ser Met Leu Gly Leu Ala Thr Ile Lys Leu Lys Ser Ile Lys Arg
    1565                1570                1575

Glu

<210> SEQ ID NO 3
<211> LENGTH: 34
<212> TYPE: DNA
<213> ORGANISM: Artificial
<220> FEATURE:
<223> OTHER INFORMATION: primer

<400> SEQUENCE: 3
catcccatgg attctgtcat aaataagcca tctg                                34

<210> SEQ ID NO 4
<211> LENGTH: 39
<212> TYPE: DNA
<213> ORGANISM: Artificial
<220> FEATURE:
<223> OTHER INFORMATION: primer

<400> SEQUENCE: 4
gcagctcgag ttctcttttg atagacttta gtttgattg                           39

<210> SEQ ID NO 5
<211> LENGTH: 36
<212> TYPE: DNA
<213> ORGANISM: Artificial
<220> FEATURE:
```

-continued

<223> OTHER INFORMATION: primer

<400> SEQUENCE: 5
atctggatcc tgattctgtc ataaataagc catctg    36

<210> SEQ ID NO 6
<211> LENGTH: 38
<212> TYPE: DNA
<213> ORGANISM: Artificial
<220> FEATURE:
<223> OTHER INFORMATION: primer

<400> SEQUENCE: 6
gccggtcgac ttattctctt ttgatagact ttagtttg    38

<210> SEQ ID NO 7
<211> LENGTH: 34
<212> TYPE: DNA
<213> ORGANISM: Artificial
<220> FEATURE:
<223> OTHER INFORMATION: primer

<400> SEQUENCE: 7
catcctcgag atcctttct tgtttgataa atac    34

<210> SEQ ID NO 8
<211> LENGTH: 36
<212> TYPE: DNA
<213> ORGANISM: Artificial
<220> FEATURE:
<223> OTHER INFORMATION: primer

<400> SEQUENCE: 8
ccggccatgg aaaacattga tagtaataaa attatc    36

<210> SEQ ID NO 9
<211> LENGTH: 34
<212> TYPE: DNA
<213> ORGANISM: Artificial
<220> FEATURE:
<223> OTHER INFORMATION: primer

<400> SEQUENCE: 9
tatactcgag tctattggaa agcagcaatt ctgc    34

<210> SEQ ID NO 10
<211> LENGTH: 33
<212> TYPE: DNA
<213> ORGANISM: Artificial
<220> FEATURE:
<223> OTHER INFORMATION: primer

<400> SEQUENCE: 10
cattccatgg tagaacacgg ggaatctggt atc    33

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
aattaaccct cactaaaggg    20

```
<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
gtaatacgac tcactatagg gc                                              22
```